United States Patent [19]

Franke

[11] 4,054,130
[45] Oct. 18, 1977

[54] EMERGENCY SPLINT ASSEMBLY

[76] Inventor: Paul William Franke, 619 Camellia St., Escondido, Calif. 92027.

[21] Appl. No.: 644,640

[22] Filed: Dec. 29, 1975

[51] Int. Cl.$^2$ ............................................. A61F 5/04
[52] U.S. Cl. ...................................... 128/87 R; 128/88
[58] Field of Search ............... 128/88, 87, 80 F, 80 R, 128/133

[56] References Cited

U.S. PATENT DOCUMENTS

| | | | |
|---|---|---|---|
| 575,199 | 1/1897 | Autenrieth | 128/88 |
| 607,666 | 7/1898 | Smith | 128/87 R |
| 1,643,850 | 9/1927 | Jones | 128/88 |
| 2,532,955 | 12/1950 | Shook | 128/80 F X |
| 2,545,843 | 3/1951 | Cohan | 128/80 F |
| 2,934,064 | 4/1960 | Invidiato | 128/80 F |
| 3,256,880 | 6/1966 | Caypinar | 128/133 |
| 3,776,225 | 12/1973 | Lonardo | 128/87 R |

*Primary Examiner*—John D. Yasko
*Attorney, Agent, or Firm*—Brown & Martin

[57] ABSTRACT

An emergency splint assembly for fractured limbs includes two limb support members releasably lockable in a multiplicity of angular orientations. At least one strap is associated with each of the limb supports. Each strap is adjustably secured in a clamp and accommodates limbs of varying girth. Each strap is also slidable along its associated limb support to accommodate a multiplicity of fracture positions.

9 Claims, 5 Drawing Figures

EMERGENCY SPLINT ASSEMBLY

BACKGROUND OF THE INVENTION

It has frequently been necessary to temporarily restrain a fractured limb until the victim is transported to a medical facility where he can be fitted with a cast. Accordingly, a variety of contrivances have been designed that are adapted to restrain fractured limbs until a more permanent restrainer is available. The devices have developed to include a variety of limb supporting members and limb restraining members interconnected in complicated and inconvenient manners. Most of the prior art devices include structure to position the limb supports in a variety of relative orientations. However, none of the prior art devices accomplish this in a convenient manner that facilitates use of the structure. A further characteristic of the prior art devices has been the incorporation of one or more strap assemblies designed to restrain the limb against the limb supports. The primary deficiency associated with such prior art devices is that the straps are not readily or conveniently adjustable to accommodate a variety of fracture points. The straps of the prior art devices are all permanently affixed to one of the limb supports, and as a consequence cannot accommodate to the variety of fracture positions that are normally encountered. Furthermore, the straps of the prior art are not easily secured and require the use of both hands to buckle them in a particular position. This, consequently, makes it relatively impossible for the victim to apply the emergency splint himself. In the case of an arm fracture, in particular situations, it is extremely desirable for an individual to be able to apply a temporary splint assembly with his one healthy hand. None of the straps of the prior art permits such manipulations and consequently restrict the use of the devices.

There has been a need, therefore, to provide an emergency splint assembly that will accompany a variety of fracture positions and limb girths. The need extends to a device that accomplishes these ends in a simple manner, with an uncomplicated and compact structure. It is also desirable that the device be appliable by the victim in the event he is isolated and he cannot otherwise obtain assistance.

SUMMARY OF THE INVENTION

In an exemplary embodiment of the invention, a pair of cooperating limb supports are pivotally connected and lockable at a multiplicity of angular orientations. The ability to pivot the limb supports renders the assembly adaptable for use with fractures at different parts of a limb and also makes it more accommodating to suit the comfort of the victim. The cooperating ends of the limb supports are stepped down into two overlapping parts, and are adjustably connected by positioning and locking means. The positioning and locking means are partly associated with each of the limb supports. One of the overlapping parts includes a male part or hinge post that is received in a female part or opening in the other member. A flat resilient washer is received between the ends and serves to separate the confronting faces thereof, and compresses under pressure. A series of stop positions or indexing holes are formed radially about the opening. A stop member or indexing pin projects from the superimposed part and is spaced from the hinge post being receivable in any of the indexing holes. The post projects below the subtending part exposing a bore. A retaining pin is received in the bore and is also received in holes forming in a securing means or cam key. A wear shield is received between the cam key and the exterior face surrounding the subtending part. To affix the assembly in a particular position, the cam key is rotated to a position adjacent the wear shield. During this movement, the washer compresses to accommodate the force exerted on the assembly by the cam key.

At least one restrainer is associated with each of the limb supports. The restrainer is in the form of a strap that is adjustable to accommodate limbs of varying girth. The strap is movably secured on the limb support by slidable means, such as a carriage that is longitudinally slidable along the limb support. The carriage is received in a track that is affixed to its associated limb support. An adjustable means, in the form of a clamp is connected to the carriage. One end of the strap is received between the clamp and the carriage and it is riveted to those members. The strap then encircles the limb support and the restrained limb, and the free end is inserted in the clamp. The clamp is in the form of an open box-shaped housing. Resilient means, such as a leaf spring, is supported in the clamp and is biased toward engagement with the free end of the strap. The leaf spring projects angularly toward the back of the clamp so that the free end of the strap can be inserted between the face of the clamp and the leaf spring. An edge of the leaf spring comprises a series of pointed teeth that engage the strap and maintain its tension. A pair of aligned longitudinal slots are formed in the sidewalls of the clamp. A movable member or pin is slidably received in the longitudinal slots sandwiching the leaf spring between the pin and the clamp housing. To release the strap from the clamp, it is merely necessary to urge the pin toward the back part of the clamp. This drives the leaf spring downwardly, disengaging it from and freeing the strap.

It is therefore an object of the invention to provide a new and improved splint assembly.

Another object of the invention is to provide a new and improved splint assembly that is securable in a multiplicity of angular orientations for accommodating a variety of limb positions.

Another object of the invention is to provide a new and improved splint assembly that straps a fractured limb securely against the limb support.

Another object of the invention is to provide a new and improved splint assembly that accommodates limbs of varying girth.

Another object of the invention is to provide a new and improved splint assembly that accommodates various fracture positions.

Another object of the invention is to provide a new and improved splint assembly that is characterized by a positive cooperation of the various structural components.

Another object of the invention is to provide a new and improved splint assembly that is compact, light in weight, durable and inexpensive.

The above and other objects of the invention will be apparent as the description continues and when read in conjunction with the appended drawings.

DETAILED DESCRIPTION OF THE DRAWINGS

Figure 1:
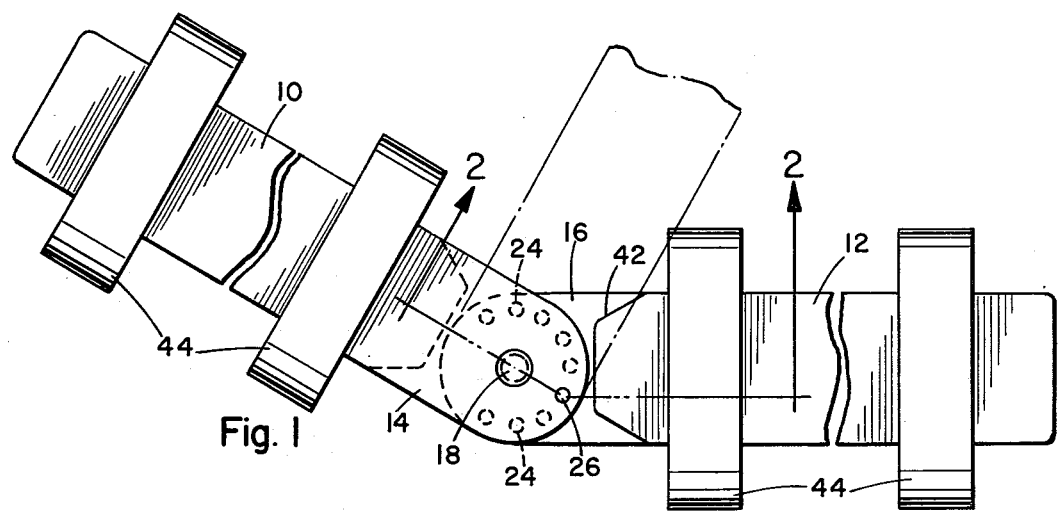
FIG. 1 is a top plan view of the splint.
Figure 2:
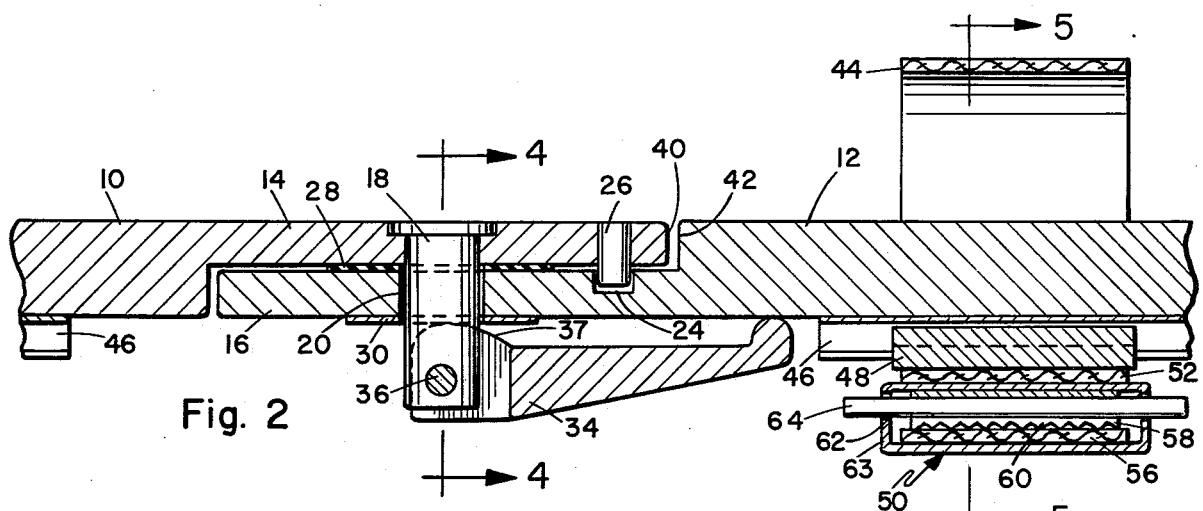
FIG. 2 is an enlarged sectional view taken on line 2—2 of FIG. 1.
Figure 3:
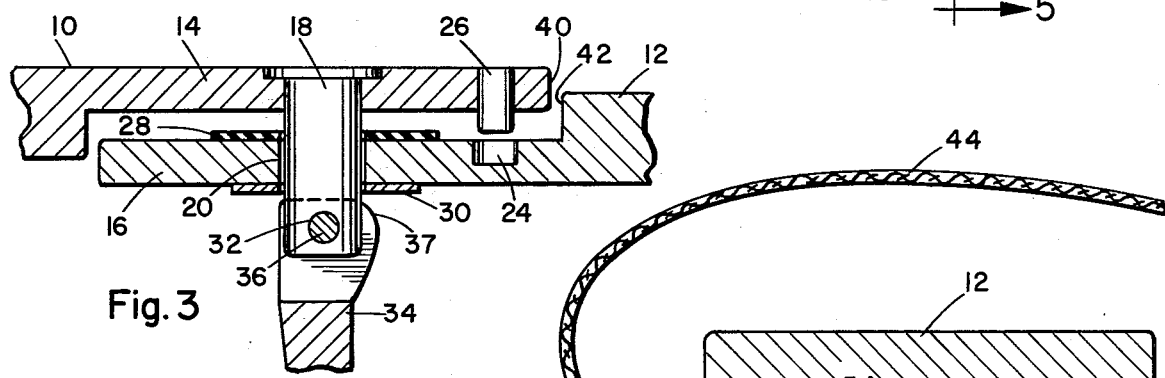
FIG. 3 is a sectional view similar to a portion of FIG. 2, but with the cam key unlocked.
Figure 4:
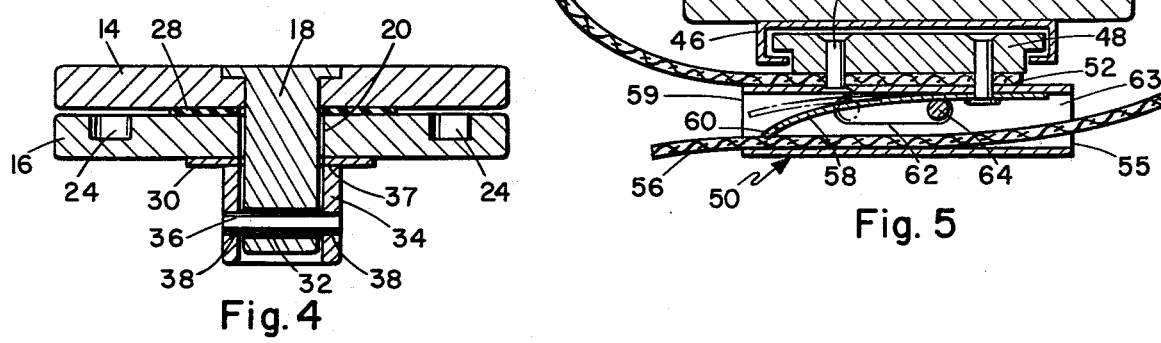
FIG. 4 is a sectional view taken on line 4—4 of FIG. 2.
Figure 5:
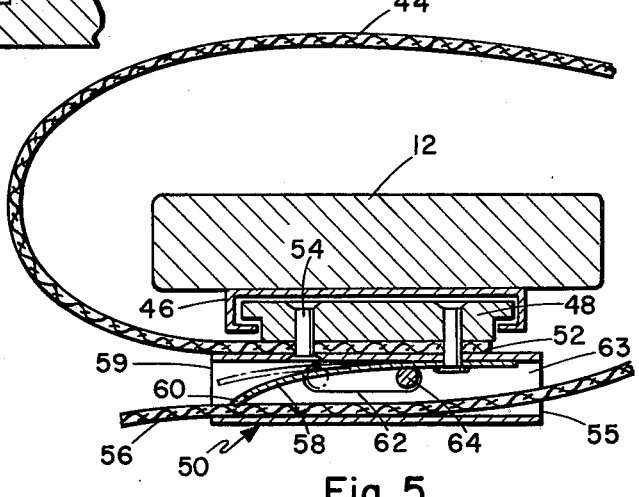
FIG. 5 is a sectional view taken on line 5—5 of FIG. 2.

In a preferred embodiment of the invention, the splint assembly comprises a pair of generally planar limb support members 10 and 12. The limb support members 10 and 12 are elongated of a length sufficient to accommodate relatively long limbs. The limb supports 10 and 12 are interconnected and are lockable at a variety of angular dispositions. This feature permits the assembly to accommodate fractures at different places along the limb, and also permits adjustment for the comfort of the victim. The interconnection between the limb supports 10 and 12 is effected by superimposing their step down ends 14 and 16. The ends 14 and 16 step down sufficiently such that when they are superimposed, the thickness corresponds to the thickness of the limb support members 10 and 12 at their outer extremities. The end 14 includes a hinge post 18 that projects downwardly toward the end 16. The post 18 is received in an opening 20 formed in the end 16. A multiplicity of stop positions in the form of indexing holes 24 are formed in the end 16 radially spaced from the opening 20. The holes 24 are smaller in diameter than the opening 20 and are adapted to receive an indexing pin 26 that projects downwardly from the interior face of the end 14. The indexing pin 26 is received in any of the holes 24 according to the desired relative orientation between the limb supports 10 and 12. It should be noted that the diameters of the opening 20 and holes 24 are slightly larger than the associated post 18 and indexing pin 26. This permits the post 18 and indexing pin 26 to be conveniently inserted and removed from opening 20 and holes 24 respectively.

The post 18 includes a bore 32. When the limb supports 10 and 12 are assembled, the post 18 protrudes beyond the exterior facing side of end 16. The protrusion is sufficient to expose the bore 32. A resilient compressible washer 28 is received about the post 18 and functions to separate the interior facing sides of the ends 14 and 16. A wear shield 30 is received about the protruding part of the post 18. A cam key 34 has a pair of aligned holes 38 formed in its respective sides. A restraining pin 36 is received through the bore 32 and into the holes 38 in the cam key 34. The cam key 34 is a forked member having two cam surfaces 37. During use, the cam key 34 is pivoted so that it lies generally parallel and adjacent the wear shield 30. During this movement, the cam surfaces 37 exert a coupling force on the ends 14 and 16, which force is accommodated by the squeezing of washer 28. The wear shield 30 prevents the exterior facing side of end 16 from being abraded or grooved during this motion. There is sufficient clearance between the respective end walls 40 and step walls 42 associated with each of the limb supports 10 and 12, to permit the two sections to conveniently pivot with respect to each other without binding or scraping.

In the preferred embodiment, a pair of restrainers or straps 44 are associated with each of the limb supports 10 and 12. The straps 44 are designed to firmly secure the sections of the limb against the associated limb supports 10 and 12. The straps 44 are movable longitudinally along the limb supports 10 and 12 so as to accommodate the fractured limb in the most convenient manner. Accordingly, a track 46 is connected to the underside of each of the limb supports 10 and 12. The track 46 accommodates a carriage 48 that is mounted for slidable movement within the track. A clamp 50 is disposed in juxtaposed relation with respect to the carriage 48. One end 52 of the strap 44 is sandwiched between carriage 48 and clamp 50. A pair of rivets 54 are received in aligned holes in the clamp 50, the strap end 52 and the carriage 48 and function to permanently secure the strap end 52 between the carriage 48 and the clamp 50. When applying the splint assembly to a victim's limb, the strap 44 is drawn from the bottom side of the limb supports 10 and 12 over the associated limb part and into the clamp 50. The clamp 50 is formed as a hollow buckle open at its front 55 and rear 59. The free end 56 of strap 44 is received through the front 55 of clamp 50. A leaf spring 58 projects rearwardly within the clamp 50 toward the end 56. The leaf spring 58 has a series of pointed teeth 60 that are designed to engage and secure the strap 44 in the limb restraining position.

When applying the assembly, the free end 56 is inserted in the clamp 50 and pushed past the leaf spring 58. It is then pulled as far past the teeth 60 as may be desired. Virtually any tension in the strap 44 is obtainable by the described structure. Furthermore, since the leaf spring 58 projects towards the strap 44, the strap 44 cannot pull out of engagement with the teeth 60 since any force tending to pull the strap 44 outwardly causes the teeth 60 to sink deeper into the strap material. To permit the strap 44 to be released from the teeth 60, a pin 64 is received in aligned slots 62 formed in the side walls 63 of the clamp 50. One end of the leaf spring 58 is juxtaposed between pin 64 and clamp 50. By pushing the pin 64 toward the rear 59 of clamp 50, the leaf spring 58 is driven to disengage the teeth 60 from the strap 44. Once disengagement has been effected, the bias of the leaf spring 58 tends to drive the pin 64 back toward the front 55 of clamp 50.

The splint of the present invention is conveniently and effectively assembled with a minimum of effort. In particular circumstances, it can even be applied by the victim if necessary. The restraint of the limb is positive and the apparatus is relatively light in weight so that it may be worn with comfort and convenience.

Modifications and adaptations in the method and materials of fabrication, in the configuration and assemblage of the constituent components are readily permissible within the scope of the present invention, which changes are intended to be embraced therewithin.

Having described my invention, I now claim:

1. An emergency splint assembly for use in restraining a fractured limb comprising:

at least two cooperating limb supports, pivotally connected and lockable in a multiplicity of relative angular positions for supporting a fractured limb, an adjustable restrainer associated with at least one of said limb supports for strapping the fractured limb against said limb supports, said restrainer being radially adjustable to accommodate limbs of varying girth, said restrainer being movable longitudinally along its associated limb support and securable at a multiplicity of stations therealong to accommodate any limb fracture position, means slidable longitudinally along at least one of said limb supports and connected to one end of said restrainer for locating said restrainer along said limb support, and adjustable means operable to releasably secure the other end of said restrainer for strapping the limb against the associated limb support, said adjustable means comprises a clamp for releasably locking the other end of said restrainer in a multiplicity of positions for accommodating limbs of varying girth, resilient means releasably mounted in said clamp, a part of said resilient means for contacting said restrainer to secure the other end thereof within said clamp, said resilient means comprises a leaf spring, said leaf spring is biased toward a restrainer securing position in which a part of said leaf spring engages said one end of said restrainer, and a movable member received in said slot and active on said leaf spring and adapted to drive the same out of engagement with said restrainer.

2. An emergency splint assembly for use in restraining a fractured limb comprising:

at least two cooperating limb support members, pivotally connected together by a pivot pin and lockable in a multiplicity of relative angular positions about a pivotal axis defined by said pivot pin for supporting a fractured limb, an adjustable strap associated with at least one of said limb support members for strapping a fractured limb against said limb support members, said strap being radially adjustable to accommodate limbs of varying girth, said strap being movable longitudinally along its associated limb support and securable at a multiplicity of stations therealong to accommodate any limb fracture position, positioning and locking means partly associated with each of said limb supports for releasably securing said limb supports in a multiplicity of relative orientations about said pivotal axis for supporting the fractured limb, and comprising an indexing pin on one of said limb support members, a plurality of indexing holes associated with the other of said limb support members said indexing pin being received in selected ones of said indexing holes for retaining said members in selected angular positions of said members and biasing means comprising lever and cam means carried by said pin for biasing said pin into selected ones of said indexing holes.

3. The splint assembly of claim 2 including:

means slidable longitudinally along at least one of said limb support member and connected to one end of said strap for locating said strap along said limb support member, and adjustable means operable to releasably secure the other end of said strap for strapping the limb against the associated limb support member.

4. The splint assembly according to claim 3 wherein:

said slidable means comprises a carriage, and a track connected to one of said limb support members, said carriage being slidably received in said track.

5. The splint assembly according to claim 3 wherein:

said adjustable means comprises a clamp for releasably locking the other end of said strap in a multiplicity of positions for accommodating limbs of varying girth.

6. The splint assembly according to claim 3 wherein:

said slidable means comprises a carriage, a track connected to one of said limb support members, said carriage being slidably received in said track, said adjustable means comprises a clamp for releasably locking the other end of said strap in a multiplicity of positions accommodating limbs of varying girth, and said one end of said strap is secured between said carriage and said clamp.

7. The splint assembly of claim 5, said adjustable means including:

resilient means releasably mounted in said clamp, a part of said resilient means for contacting said strap for securing the other end thereof within said clamp.

8. A splint assembly of claim 2 wherein said biasing means for biasing said indexing pin comprises a pin extending through said member for defining said pivotal axis, and said lever is pivotally mounted on one end of said pin for forcing said two members together along said axis.

9. The splint assembly of claim 8 wherein said lever is pivoted about an axis transverse to the axis of said pin, and said cam means is integral therewith for engaging one of said members for camming said members together.

* * * * *